United States Patent
Mackool (10) Patent No.: US 10,441,462 B1
(45) Date of Patent: Oct. 15, 2019

(54) OPHTHALMIC SURGICAL INSTRUMENTS AND METHODS OF USE THEREOF

(71) Applicant: Richard Mackool, Sarasota, FL (US)

(72) Inventor: Richard Mackool, Sarasota, FL (US)

(*) Notice: Subject to any disclaimer, the term of this patent is extended or adjusted under 35 U.S.C. 154(b) by 0 days.

(21) Appl. No.: 16/401,164

(22) Filed: May 2, 2019

Related U.S. Application Data (63) Continuation-in-part of application No. 15/970,145, filed on May 3, 2018, now Pat. No. 10,292,862.

(51) Int. Cl.
*A61F 9/007* (2006.01)
*A61B 17/32* (2006.01)
*A61F 9/013* (2006.01)

(52) U.S. Cl.
CPC ...... *A61F 9/00754* (2013.01); *A61F 9/00745* (2013.01); *A61B 17/32* (2013.01); *A61F 9/0133* (2013.01)

(58) Field of Classification Search
CPC .......... A61F 9/00754; A61F 9/00736
USPC ........................................... 606/161
See application file for complete search history.

(56) References Cited

U.S. PATENT DOCUMENTS

| | | | |
|---|---|---|---|
| 3,955,578 A | 5/1976 | Chamness | |
| 4,538,611 A | 9/1985 | Kelman | |
| 4,732,150 A * | 3/1988 | Keener, Jr. .......... | A61F 9/00736 606/107 |
| 4,766,897 A | 8/1988 | Smirmaul | |
| 4,844,065 A * | 7/1989 | Faulkner ............. | A61B 17/30 606/107 |
| 4,869,716 A | 9/1989 | Smirmaul | |
| 4,950,272 A * | 8/1990 | Smirmaul ........... | A61F 9/00736 606/107 |
| 4,960,418 A | 10/1990 | Tennant | |
| 5,098,439 A * | 3/1992 | Hill ....................... | A61F 2/1664 606/107 |
| 5,171,314 A | 12/1992 | Dulebohn | |
| 5,201,741 A | 4/1993 | Dulebohn | |
| 5,445,637 A * | 8/1995 | Bretton ............... | A61F 9/00736 604/22 |
| 6,517,550 B1 | 2/2003 | Konya | |
| 6,551,326 B1 | 4/2003 | Van Heugten | |
| 6,743,228 B2 * | 6/2004 | Lee ...................... | A61B 8/0825 606/113 |
| 8,118,862 B2 | 2/2012 | Saeed | |
| 8,252,019 B2 | 8/2012 | Fleming, III | |
| 8,814,854 B2 | 8/2014 | Jia | |
| 8,821,567 B2 | 9/2014 | Saeed | |

(Continued)

OTHER PUBLICATIONS

You Tube Video "Phaco Section by Wire Snare, by Dr. Samar K. Basak—Dlsha Eye Hospitals" Published on Jan. 30, 2013; internet address:<https://youtu.be/CP8jrVb8qrg>.

(Continued)

*Primary Examiner* — Phong Son H Dang
(74) *Attorney, Agent, or Firm* — Carter, Deluca & Farrell LLP (57) ABSTRACT

An ophthalmic surgical instrument includes a housing and a snare operably coupled to the housing. The snare is configured to transition between an insertion configuration and a deployed configuration, in which the snare is sized to encircle lenticular tissue. The ophthalmic surgical instrument is designed to prevent elevation and/or tilting of the lenticular tissue as the snare transitions toward the insertion configuration to divide the lenticular tissue.

17 Claims, 6 Drawing Sheets

(56) References Cited

U.S. PATENT DOCUMENTS

| | | | |
|---|---|---|---|
| 9,039,713 | B2 | 5/2015 | Segermark |
| 9,629,747 | B2 | 4/2017 | Clauson et al. |
| 9,775,743 | B2 | 10/2017 | Clauson et al. |
| 10,292,862 | B1 | 5/2019 | Mackool |
| 2004/0092953 | A1 | 5/2004 | Salameh |
| 2004/0092982 | A1 | 5/2004 | Sheffer |
| 2009/0054904 | A1 | 2/2009 | Holmen |
| 2009/0082787 | A1 | 3/2009 | Pang |
| 2010/0312252 | A1 | 12/2010 | Jia et al. |
| 2013/0197533 | A1 | 8/2013 | Dusek |
| 2014/0364885 | A1 | 12/2014 | Wells |
| 2015/0257927 | A1 | 9/2015 | Olson |
| 2016/0143778 | A1 | 5/2016 | Aljuri |
| 2016/0346121 | A1 | 12/2016 | Ianchulev |
| 2017/0312125 | A1 | 11/2017 | Clauson et al. |
| 2018/0036170 | A1* | 2/2018 | Ghannoum ......... A61F 9/00763 |
| 2018/0036171 | A1 | 2/2018 | Clauson et al. |
| 2018/0064578 | A1 | 3/2018 | Clauson |
| 2018/0318132 | A1 | 11/2018 | Clauson |
| 2018/0318133 | A1 | 11/2018 | Clauson |

OTHER PUBLICATIONS

Bhattacharya, "Nuclear management in manual small incision cataract surgery by snare technique", Indian J. Ophthalmology, Feb. 2009, vol. 57, No. 1; 11 pages.

International Search Report dated Jul. 12, 2019, issued in International Appln. No. PCT/US19/29588.

* cited by examiner

OPHTHALMIC SURGICAL INSTRUMENTS AND METHODS OF USE THEREOF

CROSS-REFERENCE TO RELATED APPLICATION

This application is a continuation-in-part of U.S. patent application Ser. No. 15/970,145, filed on May 3, 2018, the entire contents of which are incorporated by reference herein.

BACKGROUND

Technical Field

The present disclosure relates to ophthalmic surgical instruments, and more particularly, to ophthalmic surgical instruments and methods that facilitate the fragmentation and removal of a lens from a lens capsule.

Background of Related Art

Cataract surgery and other surgical procedures that treat lenticular tissue, such as, for example, the intraocular lens, are performed by making a small incision in the edge of the cornea, which provides access to the anterior chamber and to the anterior surface of the lens capsule. Afterward, a generally circular incision called a capsulorhexis is made through the anterior surface of the lens capsule to provide surgical access to the lens. An ophthalmic surgical instrument may be inserted through the capsulorhexis and used to fragment the cataractous lens to facilitate its removal from the lens capsule. However, during segmentation by the surgical instrument, the distal portion of the lens may be caused to shift undesirably in an upward (i.e., anterior) direction. Such movement may cause trauma to delicate adjacent eye structures such as the lens zonule, lens capsule or, corneal endothelium.

Accordingly, a continuing need exists in the surgical arts for improved tools and methods for safely fragmenting and removing a cataractous lens.

SUMMARY

In accordance with an aspect of the present disclosure, an ophthalmic surgical instrument for severing a lens of an eye is provided and includes an elongated shaft, and a snare. The elongated shaft includes a proximal end portion and a distal end portion defining an opening. The distal end portion is offset from the proximal end portion. The snare extends along the elongated shaft and includes a cutting segment disposed adjacent the opening. The cutting segment is configured to move between a contracted configuration and a dilated configuration, in which the cutting segment assumes a diameter approximating a diameter and shape of a lens. The cutting segment is configured to sever the lens upon moving toward the contracted configuration.

In aspects, the elongated shaft may further include an intermediate portion extending between the proximal and distal end portions. The intermediate portion may be angled relative to the proximal and distal end portions.

In aspects, the elongated shaft may have a bent proximal segment and a bent distal segment. The intermediate portion may extend between the bent proximal and distal segments.

In aspects, the intermediate segment may be curved or linear.

In aspects, the proximal end portion may define a first longitudinal axis, the distal end portion may define a second longitudinal axis that is parallel with the first longitudinal axis, and the intermediate portion may define a third longitudinal axis that is non-parallel with respect to the first and second longitudinal axes.

In aspects, the proximal end portion may define a first longitudinal axis and the distal end portion may define a second longitudinal axis that is parallel and out of alignment with the first longitudinal axis.

In aspects, the distal end portion may have a length from about 3.5 mm to about 12 mm.

In aspects, distal end portion may have a length of about 6 mm.

In aspects, the distal end portion may have a bottom portion configured to be oriented toward a human eye, and an upper portion. The bottom portion may define the opening therein.

In aspects, the upper portion may have a concave inner surface overlapping the looped segment and the opening.

In aspects, the opening may have a length that is less than about half of a length of the cutting segment when the cutting segment is in the dilated configuration.

In aspects, a majority of the length of the cutting segment may be disposed proximally and distally of the opening when the cutting segment is in the dilated configuration.

In accordance with another aspect of the present disclosure, an ophthalmic surgical instrument for severing a lens of an eye is provided and includes a handle, an elongated shaft extending distally from the handle, and a snare coupled to the housing. The elongated shaft includes a distal end portion defining an opening. The distal end portion is angled relative to a proximal portion of the elongated shaft that is disposed proximally of the distal end portion. The snare is operably coupled to the housing and includes a looped segment configured to move between a contracted configuration and a dilated configuration. In the dilated configuration, the looped segment assumes a diameter approximating a diameter and shape of a lens. The looped segment is configured to sever the lens upon moving toward the contracted configuration.

In aspects, the distal end portion may be bent relative to the proximal portion.

In aspects, the proximal portion may include a proximal end portion coupled to the handle, and an intermediate portion disposed between and interconnecting the proximal end portion and the distal end portion.

In aspects, the distal end portion may be bent relative to the intermediate portion.

In aspects, the intermediate portion may be bent relative to the proximal end portion in an opposite direction as the distal end portion is bent relative to the intermediate portion.

In aspects, the opening may have a length that is less than about half of a length of the looped segment when the looped segment is in the dilated configuration.

In aspects, a majority of the length of the looped segment may be disposed proximally and distally of the opening when the looped segment is in the dilated configuration.

Further details and aspects of exemplary embodiments of the present disclosure are described in more detail below with reference to the appended figures.

As used herein, the terms parallel and perpendicular are understood to include relative configurations that are substantially parallel and substantially perpendicular up to about + or −25 degrees from true parallel and true perpendicular.

As used herein, the term "about" means that the numerical value is approximate and small variations would not significantly affect the practice of the disclosed embodiments. Where a numerical limitation is used, unless indicated otherwise by the context, "about" means the numerical value can vary by ±10% and remain within the scope of the disclosed embodiments.

BRIEF DESCRIPTION OF THE DRAWINGS

Embodiments of the present disclosure are described herein with reference to the accompanying drawings, wherein.

DETAILED DESCRIPTION

Embodiments of the presently disclosed ophthalmic surgical instruments are described in detail with reference to the drawings, in which like reference numerals designate identical or corresponding elements in each of the several views. As used herein and as is traditional, the term "distal" will refer to that portion of the ophthalmic surgical instrument which is further from the user (i.e., closer to the eye) while the term "proximal" will refer to that portion of the ophthalmic surgical instrument which is closer to the user (i.e., further from the eye).

The present disclosure provides embodiments of an ophthalmic surgical instrument used to fragment cataractous lenticular tissue prior to its removal from a lens capsule. The ophthalmic surgical instrument includes a handle portion, a snare for enclosing and severing the lenticular tissue, and a pair of stabilization elements that are selectively extendable outwardly relative to the snare during actuation of the snare. The stabilization elements may be any suitable structure that extends outwardly from the distal end or from opposite sides of the snare to overlay opposing sides of the lenticular tissue during its division by the snare. As the snare is contracted about the lenticular tissue, the stabilization elements resist anterior shifting (i.e., upward shifting) of the lenticular tissue, which may otherwise occur due to the proximally-oriented force exerted on the lenticular tissue during contraction of the snare. In some embodiments, the ophthalmic surgical instrument is constructed so that a distally-extending cannula thereof acts as the stabilization element. These and other features and advantages of the various embodiments of the disclosed ophthalmic surgical instruments will be described below.

With reference to FIGS. 1A-3C, an exemplary embodiment of an ophthalmic surgical instrument is illustrated and is generally designated 100. The ophthalmic surgical instrument 100 generally includes a housing 110, a snare 112 for severing lenticular tissue, and a pair of stabilization elements, such as, for example, elongated arms 120, 122 that selectively expand from a closed or collapsed configuration (FIGS. 1A, 2A, 3A) to an open or expanded configuration (FIGS. 1B, 2B, 3B).

Figure 1A:
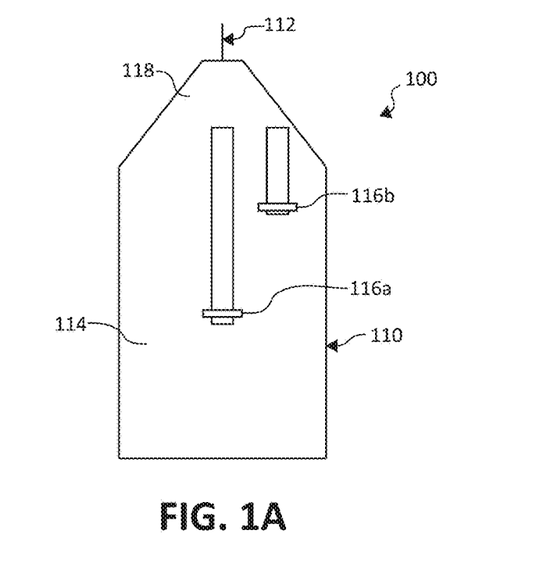
FIG. 1A is a top view of an ophthalmic surgical instrument in accordance with an embodiment of the present disclosure, illustrating a snare thereof in a contracted configuration.
Figure 1B:
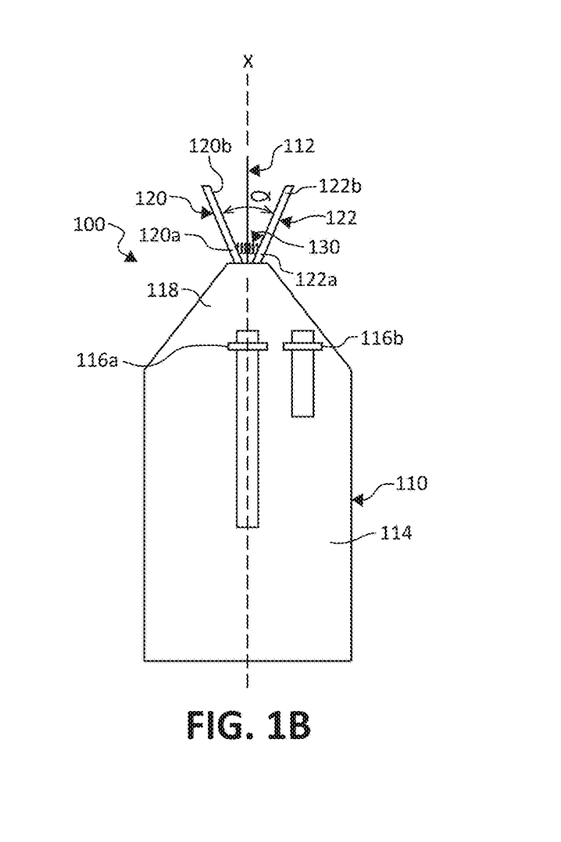
FIG. 1B is a top view of the ophthalmic surgical instrument of FIG. 1A, illustrating the snare in a dilated configuration and a pair of stabilization elements in an open configuration.

The housing 110 of the ophthalmic surgical instrument 100 has a handle body 114 and first and second levers 116a, 116b slidably coupled to the handle body 114. The handle body 114 may be ergonomic and have an elongated configuration. In embodiments, the handle body 114 may assume any suitable shape, such as, for example, rounded, planar, rectangular, or the like. The handle body 114 has a tapered distal end portion 118 dimensioned to assist in positioning the ophthalmic surgical instrument 100 adjacent eye structure. The levers 116a, 116b may be configured as sliders, buttons, triggers, or the like. In embodiments, the housing 110 may include a cannulated member, such as, for example, a hollow shaft (not shown), extending distally from the distal end portion 118 of the handle body 114 to facilitate entry of the ophthalmic surgical instrument 100 through a standard corneal incision.

Figure 2A:
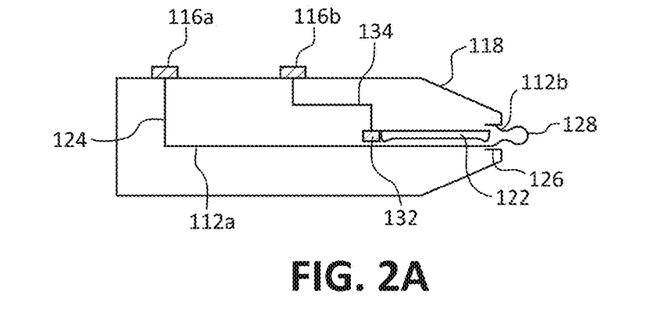
FIG. 2A is a side cross-sectional view of the ophthalmic surgical instrument of FIG. 1A, illustrating the snare in the contracted configuration and the stabilization elements in the closed configuration.
Figure 2B:
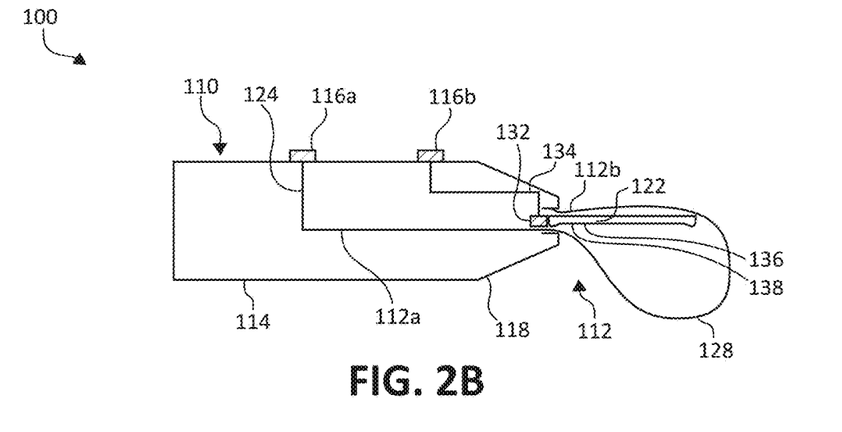
FIG. 2B is a side cross-sectional view of the ophthalmic surgical instrument of FIG. 1A, illustrating the snare in the dilated configuration and the stabilization elements in the open configuration.

The snare 112 of the ophthalmic surgical instrument 100 is operably coupled to the first lever 116a of the housing 110 and includes a first end portion 112a and a second end portion 112b (FIGS. 2A and 2B). The first end portion 112a of the snare 112 is movable relative to the housing 110, while the second end portion 112b of the snare 112 is fixed relative to the housing 110. In particular, the first end portion 112a of the snare 112 is coupled to the first lever 116a of the housing via a first actuator rod 124, such that movement of the first lever 116a moves the first end portion 112a of the snare 112, and the second end portion 112b of the snare 112 is fixed to an inner tubular structure 126 (FIGS. 3A and 3B) formed in the distal end portion 118 of the handle body 114. It is contemplated that the second end portion 112b of the snare 112 may be fixed to the inner tubular structure 126 of the handle body 114 by crimping, welding, adhesives, mechanical interlocks, or any other suitable structure or method.

Figure 3A:
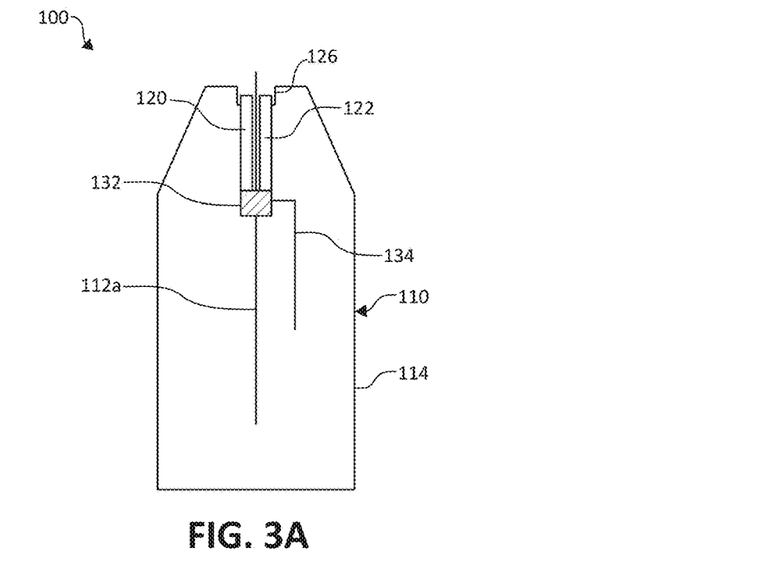
FIG. 3A is a top cross-sectional view of the ophthalmic surgical instrument of FIG. 1A, illustrating the snare in the contracted configuration and the stabilization elements in the closed configuration.
Figure 3B:
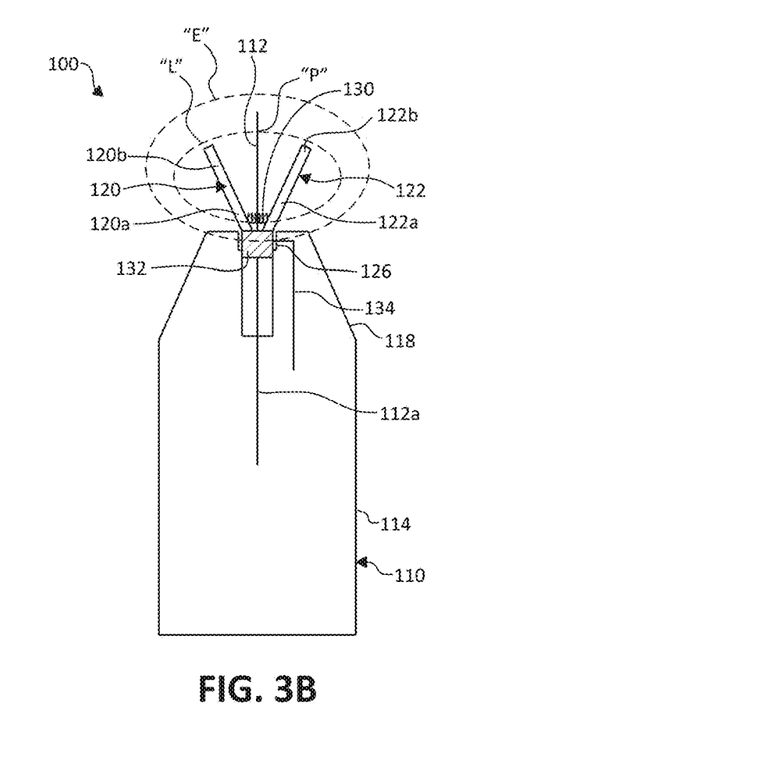
FIG. 3B is a top cross-sectional view of the ophthalmic surgical instrument of FIG. 1A, illustrating the snare in the dilated configuration and the stabilization elements in the open configuration.

With reference to FIGS. 2A and 2B, the snare 112 has a looped segment 128 disposed at least partially outside of the housing 110. The looped segment 128 of the snare 112 is transitionable, via an actuation of the first lever 116a, between an insertion or contracted configuration, as shown in FIGS. 1A, 2A, and 3A, and a deployed or dilated configuration, as shown in FIGS. 1B, 2B, and 3B. For example, a proximal retraction of the first lever 116a moves the first end portion 112a of the snare 112 proximally away from the second end portion 112b of the snare 112, thereby reducing the diameter of the looped segment 128. In contrast, a distal advancement of the first lever 116a moves the first end portion 112a of the snare 112 distally toward the second end portion 112b of the snare 112, thereby increasing the diameter of the looped segment 128 of the snare 112. The looped segment 128 has a predefined shape dimensioned to closely encircle a lens when the looped segment 128 is in the dilated configuration.

In embodiments, at least the looped segment 128 of the snare 112 may be a metal or polymer wire, tether, strap, belt, or the like, with any suitable cross-section configuration configured to sever lenticular tissue during contraction of the looped segment 128 about the lenticular tissue.

For an exemplary description of further features of the snare 112 and the mechanism of its operation, reference may be made to U.S. Pat. No. 9,775,743, filed on Sep. 17, 2014, the entire contents of which being incorporated by reference herein.

With continued reference to FIGS. 1B and 2A-3B, the stabilization elements or arms 120, 122 of the ophthalmic surgical instrument 100 are disposed on opposite sides of a longitudinal axis "X" defined by the snare 112. The arms 120, 122 are configured to move from the closed configuration (FIGS. 1A, 2A, 3A) to the open configuration (FIGS. 1B, 2B, 3B) to maintain lenticular tissue in its current location, typically but not always within its lens capsule, as will be described. In embodiments, the arms 120, 122 may be configured to move independently of one another. The arms 120, 122 are illustrated as being linear, but it is contemplated that the arms 120, 122 may assume any suitable shape, such as, for example, wing-shaped, disc-shaped, plate-like, or polygonal.

The arms 120, 122 may be resiliently-biased toward the open configuration by a biasing member, such as, for example, a coil spring 130, disposed therebetween. As such, upon moving the arms 120, 122 distally out of the handle body 114 or the hollow shaft (not shown) of the housing 110, the arms 120, 122 automatically expand outwardly relative to one another. The arms 120, 122 each have a proximal end portion 120a, 122a pivotably coupled to a hub 132, and a distal end portion 120b, 122b. In other embodiments, instead of being pivotable, the arms 120, 122 may be configured to shift laterally outward from the collapsed configuration to the expanded configuration.

The hub 132 couples the arms 120, 122 to the second lever 116b of the housing 110. In particular, the housing 110 has a second actuator rod 134 interconnecting the hub 132 and the second lever 116b. Upon sliding the second lever 116b relative to the handle body 114, the second actuator rod 134 transfers the sliding motion to the hub 132 to axially move the arms 120, 122 along the longitudinal axis "X" of the snare 112 relative to the handle body 114 between a proximal position and a distal position. In the proximal position, the arms 120, 122 are concealed within the inner tubular structure 126 of the handle body 110 or the hollow shaft when the hollow shaft is used. With the arms 120, 122 disposed within the housing 110, the inner tubular structure 126 of the handle body 119 (or the hollow shaft when used) maintains the arms 120, 122 in the collapsed configuration, in which the arms 120, 122 are parallel with one another and the longitudinal axis "X" of the snare 112, therefore assuming a reduced profile. Upon moving the arms 120, 122 toward the distal position, the arms 120, 122 move distally out of the housing 110 (the handle body 114 and/or the hollow shaft when used) allowing the outwardly-oriented bias of the biasing member 130 to transition the arms 120, 122 toward the expanded configuration. In embodiments, rather than automatically moving toward the expanded configuration upon exiting the housing 110, the arms 120, 122 may be expanded manually via a drive mechanism (not shown).

As shown in FIGS. 1B and 3B, in the expanded configuration, the arms 120, 122 flare outwardly from opposite sides of the snare 112 to define an angle α between the arms 120, 122. In embodiments, the angle α may be between about 0.1 degrees and about 180 degrees. In embodiments, the angle α may be between about 10 degrees and about 90 degrees.

The arms 120, 122 together define and reside in a horizontal plane, and the expanded looped segment 128 of the snare 112 defines and resides in a vertical plane that is aligned with the longitudinal axis "X" of the snare 112. The arms 120, 122 remain the horizontal plane throughout their movement between the collapsed and expanded configurations. The arms 120, 122 are parallel with the longitudinal axis "X" of the snare 112 while the horizontal plane of the arms 120, 122 is perpendicular relative to the vertical plane of the looped segment 128 of the snare 112.

In embodiments, the arms 120, 122 may be axially movable in a direction perpendicular to the horizontal plane of the looped segment 128 to adjust a vertical position of the arms 120, 122 relative to the housing 110 as well as lenticular tissue. For example, the housing 110 may further include a third lever (not shown) coupled to the hub 132 for moving the arms 120, 122 vertically relative to the housing 110.

As best shown in FIGS. 2A and 2B, each of the arms 120, 122 has a posterior tissue-contacting surface 136. The posterior tissue-contacting surface 136 of the arms 120, 122 may define an arcuate recess 138 therein dimensioned to conform to an anterior surface of a lens of an eye. As such, upon deploying the arms 120, 122 over a lens, the posterior tissue-contacting surface 136 of each of the arms 120, 122 cups the anterior surface of the lens, thereby providing increased surface contact between the arms 120, 122 and the lens. It is contemplated that the posterior tissue-contacting surface 136 may have a coating or liner of pliable material, such as an elastomer to help protect vulnerable structures in the eye.

In operation, a small incision in the edge of a cornea is made to provide access to an anterior chamber and an anterior surface of a cataractous lens of a patient's eye "E" (FIG. 3B). A capsulorhexis is made through the anterior surface of a lens capsule of the patient's eye "E," thereby providing surgical access to the cataractous lens "L." With the arms 120, 122 of the ophthalmic surgical instrument 100 disposed in the proximal position within the housing 110, and the snare 112 in the insertion configuration, as shown in FIGS. 2A and 3A, the hollow shaft of the housing 110 is inserted through the corneal incision and the capsulorhexis to position the looped segment 128 of the snare 112 adjacent the anterior surface of the lens "L." Once in position, the first lever 116a is advanced to move the first end portion 112a of the snare 112 distally, thereby transitioning the looped segment 128 from the insertion configuration to the deployed configuration, as shown in FIG. 2B. With the looped segment 128 in the deployed configuration, the snare 112 is rotated about its longitudinal axis "X" (e.g., via rotation of the entire ophthalmic surgical instrument 100 or via a rotation mechanism (not shown) coupled to the snare 112) to rotate the looped segment 128 circumferentially about the lens to encircle the lens and position the looped segment 128 so that the vertical plane defined by the looped segment 128 bisects the lens.

With the looped segment 128 of the snare 112 in the selected position noted above, the second lever 116b of the housing 110 may be advanced to move the arms 120, 122 from the proximal position to the distal position. As noted above, as the arms 120, 122 move to the distal position, the arms 120, 122 automatically transition from the closed configuration to the open configuration, as shown in FIGS. 1B and 3B. More specifically, the arms 120, 122 move distally along the anterior surface of the lens "L" while also expanding relative to one another and the longitudinal axis "X" of the snare 112 to position the posterior tissue-contacting surface 136 (FIG. 2B) of each of the arms 120, 122 over lateral side portions of the anterior surface of the lens "L."

With the arms 120, 122 overlaying and in contact with the anterior surface of the lens "L," the first lever 116a may then be retracted to transition the looped segment 128 from the dilated configuration to the contracted configuration, dividing the lens "L" into two hemispherical sections. During constriction of the looped segment 128 about the lens "L," the looped segment 128 may exert a proximally-oriented and/or anteriorly oriented force on a distal pole "P" of the lens "L." However, since the arms 120, 122 are in position over the lens "L," the arms 120, 122 resist and/or prevent the distal pole "P" of the lens "L" from shifting proximally out of the lens capsule notwithstanding the proximally-oriented force exerted thereon by the snare 112.

After one or more fragmentations of the lens "L" by the ophthalmic surgical instrument 100, the fragmented sections of the cataractous lens "L" may then be removed from the eye "E" using any suitable mechanism, such as, for example, an ultrasonic aspirator.

In some embodiments, the snare 112 and/or the arms 120, 122 may be mechanically powered through an electric motor, a pneumatic power source, a hydraulic power source, magnets, or the like. It is also contemplated that the ophthalmic surgical instrument 100 may be incorporated into a robotic surgical system.

Figure 4A:
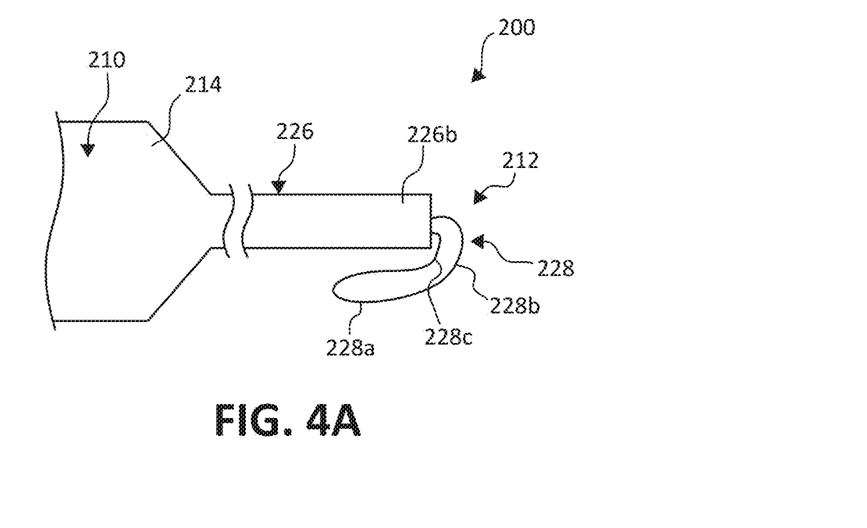
FIG. 4A is a side view of another embodiment of an ophthalmic surgical instrument, illustrating a snare thereof in a contracted configuration.
Figure 4B:
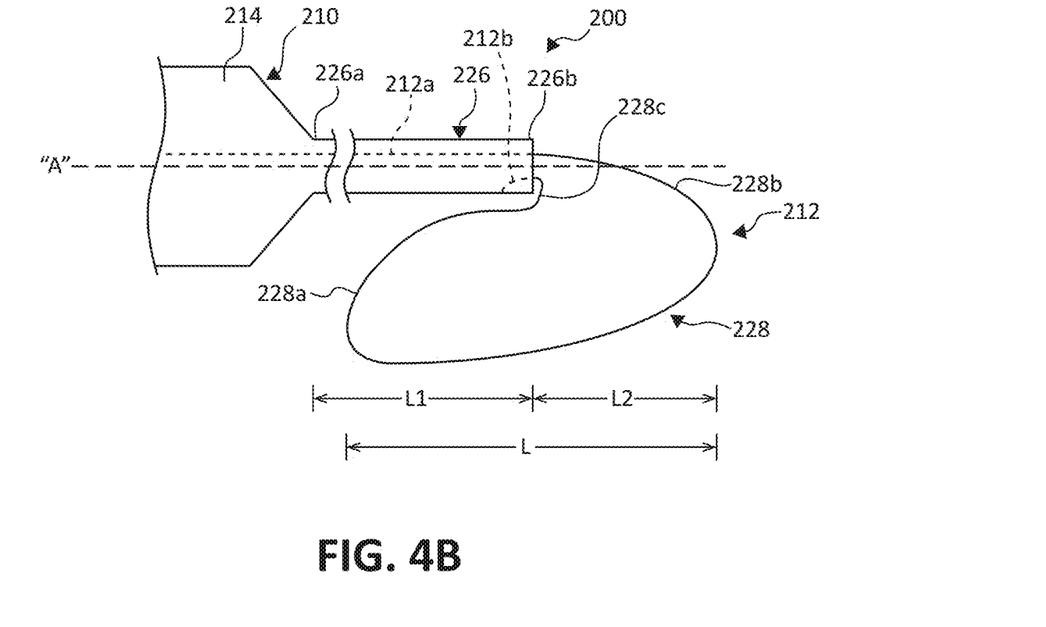
FIG. 4B is a side view of the ophthalmic surgical instrument of FIG. 4A, illustrating the snare in a dilated configuration.

With reference to FIGS. 4A and 4B, another embodiment of an ophthalmic surgical instrument 200 is illustrated, similar to the ophthalmic surgical instrument 100 described above. Due to the similarities between the ophthalmic surgical instrument 200 of the present embodiment and the ophthalmic surgical instrument 100 described above, only those elements of the ophthalmic surgical instrument 200 deemed necessary to elucidate the differences from ophthalmic surgical instrument 100 described above will be described in detail.

The ophthalmic surgical instrument 200 generally includes a housing 210 and a snare 212 for severing lenticular tissue. The housing 210 of the ophthalmic surgical instrument 200 has a handle body 214 and a cannulated body, such as, for example, a hollow shaft 226 extending distally from the handle body 214. The hollow shaft 226 is dimensioned for passage through a corneal incision and has a proximal end 226a integrally formed with or attached to the handle body 214.

The snare 212 of the ophthalmic surgical instrument 200 includes a first end portion 212a and a second end portion 212b. The first end portion 212a of the snare 212 is movable relative to and within the hollow shaft 226 of the housing 210 via an actuation mechanism (not shown), while the second end portion 212b of the snare 212 is fixed relative to the housing 210. It is contemplated that the first end portion 212a of the snare 212 may be axially movable within the hollow shaft 226 via any suitable actuation mechanism, such as, for example, manual actuation or any suitable motorized actuation mechanism. The second end portion 212b of the snare 212 may be fixed to an inner surface of the hollow shaft 226 by crimping, welding, adhesives, mechanical interlocks, or any other suitable structure or method.

The snare 212 has a looped segment 228 disposed protruding out of a distal end 226b of the hollow shaft 226. The looped segment 228 of the snare 212 is transitionable, via axial movement of the first end portion 212a of the snare 212, between an insertion or contracted configuration, as shown in FIG. 4A, and a deployed or dilated configuration, as shown in FIG. 4B. For example, a proximal retraction of a lever (not shown) of the housing 210 moves the first end portion 212a of the snare 212 proximally away from the second end portion 212b of the snare 212, thereby reducing the diameter of the looped segment 228. In contrast, a distal advancement of the lever moves the first end portion 212a of the snare 212 distally toward the second end portion 212b of the snare 212, thereby increasing the diameter of the looped segment 228 of the snare 212. The looped segment 228 has a predefined shape dimensioned to closely encircle a lens when the looped segment 228 is in the dilated configuration.

The looped segment 228 of the snare 212 differs from the looped segment 128 of the snare 112 of the ophthalmic surgical instrument 100 of FIGS. 1A-3B in that a majority of the looped segment 228 overlaps with the housing 210 (e.g., the hollow shaft 226) rather than a majority of the looped segment 228 being disposed distally of the housing 210. The looped segment 228 has a proximal section 228a having a predefined curvature, and a distal section 228b having a predefined curvature. The distal section 228b of the looped segment 228 is disposed distally of the distal end 226 of the hollow shaft 226, and the proximal section 228a of the looped segment 228 is disposed below the hollow shaft 226 and proximally of the distal end 226b of the hollow shaft 226.

The looped segment 228 further includes a pre-bent section 228c extending from the second end portion 212b of the snare 212. The pre-bent section 228c is disposed distally and outside of the housing 210 and has a smaller radius of curvature relative to the proximal and distal sections 228a, 228b of the looped segment 228 to position the proximal section 228a of the looped segment 228 proximally of and underneath the distal end 226 of the hollow shaft 226 of the housing 210. The proximal section 228a, the distal section 228b, and the pre-bent section 228c of the looped segment 228 may be fabricated from the same material or different materials. For example, the pre-bent section 228c may be fabricated from a less flexible material than the proximal and distal sections 228a, 228b of the looped segment 228 to ensure that a majority of the looped segment 228 overlaps with the hollow shaft 226 throughout the transition of the looped segment 228 between the contracted and dilated configurations.

The looped segment 228 defines a length "L" parallel with a central longitudinal axis "A" defined by the hollow shaft 226. The proximal section 228a of the looped segment 228 has a length "L1," which is approximately ½ or more of the overall length "L" of the looped segment 228, and the distal section 228b of the looped segment 228 has a length "L2," which is less than ½ of the overall length of the looped segment 228. In embodiments, the length "L1" of the proximal section 228a of the looped segment 228 is approximately ¾ of the overall length "L" of the looped segment 228, and the distal section 228b of the looped segment 228 has a length "L2," which is approximately ¼ of the overall length "L" of the looped segment 228. In this way, during use of the ophthalmic surgical instrument 200, a majority of the looped segment 228 overlaps with the housing 210 (e.g., the hollow shaft 226), such that the housing 210 is configured to rest on lenticular tissue during its fragmentation to prevent upward movement thereof during constriction of the looped segment 228.

The looped segment 228 is fabricated from shape memory materials, such as, for example, a nickel-titanium alloy to allow the looped segment 228 to move to its predefined, dilated configuration. Other shape memory materials, such as shape memory plastics are also contemplated. In other embodiments, the looped segment 228 may be fabricated from any suitable biocompatible material including, but not limited to, stainless steel, titanium, silicone, polyimide, polyether block amide, nylon, polycarbonate, or combinations thereof.

In operation, a small incision in the edge of a cornea is made to provide access to an anterior chamber and an anterior surface of a cataractous lens of a patient's eye. A capsulorhexis is made through the anterior surface of a lens capsule of the patient's eye providing surgical access to the cataractous lens. With the snare 212 of the ophthalmic surgical instrument 200 in the insertion configuration, as shown in FIG. 4A, the hollow shaft 226 of the housing 210 is inserted through the corneal incision and the capsulorhexis to position a distal end portion of the hollow shaft 226 in an overlapping arrangement with the anterior surface of the lens, and position the looped segment 228 of the snare 212 adjacent the anterior surface of the lens.

Once the looped segment 228 is in the appropriate position, the first end portion 212a of the snare 212 is advanced distally, thereby transitioning the looped segment 228 from the insertion configuration to the deployed configuration, as shown in FIG. 4B. With the looped segment 228 in the deployed configuration, the snare 212 is rotated about its longitudinal axis "A" (e.g., via rotation of the entire ophthalmic surgical instrument 200 or via a rotation mechanism (not shown)) to rotate the looped segment 228 circumferentially about the lens to encircle the lens and position the looped segment 228 relative to the lens so that the plane defined by the looped segment 228 bisects the lens. Upon rotating the snare 212 to the selected position, the distal end portion of the hollow shaft 226 overlaps with the anterior surface of the lens and a majority of the looped segment 228 of the snare 212.

With the looped segment 228 of the snare 212 disposed about the lens, and the distal end portion of the hollow shaft 226 overlaying and in contact with the anterior surface of the lens, the looped segment 228 is transitioned from the dilated configuration to the contracted configuration, dividing the lens into two hemispherical sections. During constriction of the looped segment 228 about the lens, the looped segment 228 may exert a proximally-oriented and/or anteriorly-oriented force on a distal pole of the lens. However, since the distal end portion of the hollow shaft 226 is in position over the lens, the hollow shaft 226 resists and/or prevents elevation and/or tilting of the distal pole of the lens notwithstanding the proximally-oriented force exerted thereon by the closing snare 212.

After one or more fragmentations of the lens by the ophthalmic surgical instrument 200, the fragmented sections of the cataractous lens may then be removed from the eye using any suitable mechanism, such as, for example, an ultrasonic aspirator.

Figure 5A:
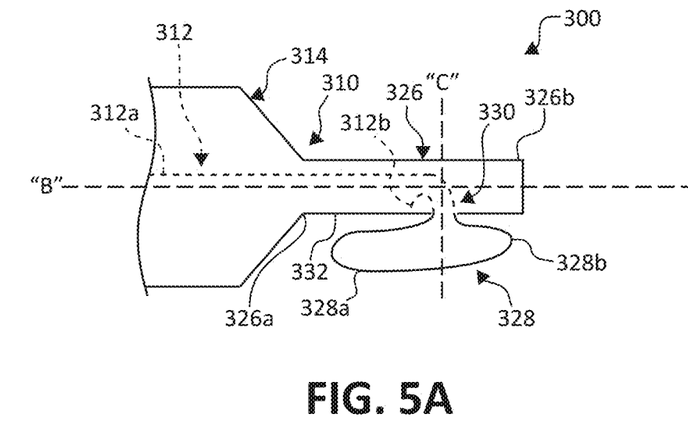
FIG. 5A is a side view of yet another embodiment of an ophthalmic surgical instrument, illustrating a snare thereof in a contracted configuration.
Figure 5B:
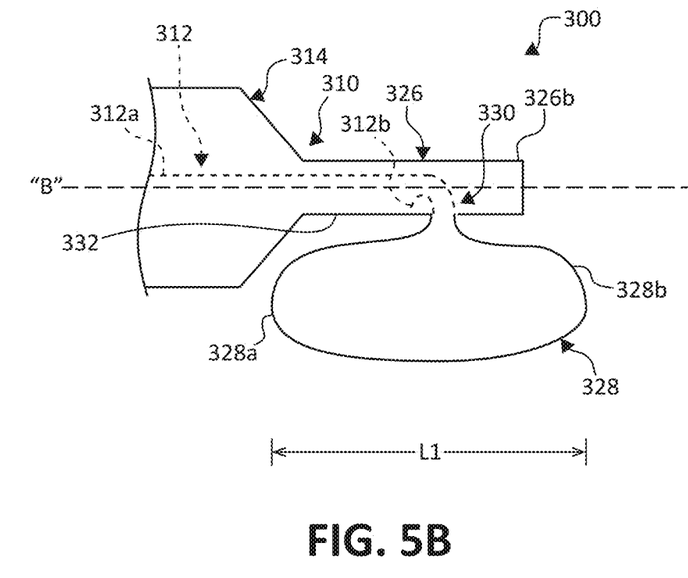
FIG. 5B is a side view of the ophthalmic surgical instrument of FIG. 5A, illustrating the snare in a dilated configuration.

With reference to FIGS. 5A and 5B, another embodiment of an ophthalmic surgical instrument 300 is illustrated, similar to the ophthalmic surgical instrument 200 described above. Due to the similarities between the ophthalmic surgical instrument 300 of the present embodiment and the ophthalmic surgical instrument 200 described above, only those elements of the ophthalmic surgical instrument 300 deemed necessary to elucidate the differences from ophthalmic surgical instrument 200 described above will be described in detail.

The ophthalmic surgical instrument 300 generally includes a housing 310 and a snare 312 operably coupled to the housing 310 for severing lenticular tissue. The housing 310 of the ophthalmic surgical instrument 300 has a handle body 314 and a cannulated body, such as, for example, a hollow shaft 326 extending distally from the handle body 314. The hollow shaft 326 is dimensioned for passage through a corneal incision and has a proximal end 326a integrally formed with or attached to the handle body 314, and a closed distal end 326b. In embodiments, the distal end 326b of the hollow shaft 326 may be open. The hollow shaft 326 defines a central longitudinal axis "B" and defines a lateral opening 330 in a lateral side surface 332 thereof. The lateral opening 330 is laterally offset from the central longitudinal axis "B" and defines an axis "C" therethrough that is perpendicular to the central longitudinal axis "A" of the hollow shaft 326. The lateral opening 330 may be any suitable shape, such as, for example, circular, elongated, square, or the like.

The snare 312 of the ophthalmic surgical instrument 300 includes a first end portion 312a and a second end portion 312b. The first end portion 312a of the snare 312 is movable relative to and within the hollow shaft 326 of the housing 310 via an actuation mechanism (not shown), similar to the actuation mechanism described above, while the second end portion 312b of the snare 312 is fixed relative to the housing 310. The second end portion 312b of the snare 312 may be fixed to an inner surface of the hollow shaft 226 by crimping, welding, adhesives, mechanical interlocks, or any other suitable structure or method. In other embodiments, both the first and second end portions 312a, 312b may be axially movable.

The snare 312 has a looped segment 328 protruding out of the lateral opening 330 in the lateral side 332 of the hollow shaft 226. The looped segment 328 of the snare 312 is transitionable, via axial movement of the first end portion 312a of the snare 312, between an insertion or contracted configuration, as shown in FIG. 5A, and a deployed or dilated configuration, as shown in FIG. 5B. For example, a proximal retraction of a lever (not shown) of the housing 310 moves the first end portion 312a of the snare 312 proximally away from the second end portion 312b of the snare 312, thereby reducing the diameter of the looped segment 328. In contrast, a distal advancement of the lever moves the first end portion 312a of the snare 312 distally toward the second end portion 312b of the snare 312, thereby increasing the diameter of the looped segment 328 of the snare 312. The looped segment 328 has a predefined shape dimensioned to closely encircle a lens when the looped segment 328 is in the dilated configuration. In embodiments, both the first and second end portions 312a, 312b of the snare 312 may be movable to contract or dilate the looped segment 328.

The looped segment 328 defines a length "L" parallel with a central longitudinal axis "B" defined by the hollow shaft 326. A majority of the length "L" of the looped segment 328 is in side-by-side, parallel relation with the lateral side 332 of the hollow shaft 326. Further, a majority of the looped segment 328 (i.e., at least half) is disposed proximally of the distal end 326b of the hollow shaft 326. In this way, during use of the ophthalmic surgical instrument 300, the hollow shaft 326 hangs over a majority of the looped segment 328, such that the hollow shaft 326 sits on a lens during lens fragmentation to prevent upward movement of the lens as the looped segment 328 is constricted thereabout.

The looped segment 328 includes a proximal section 328a disposed proximally of the lateral opening 330, and a distal section 328b disposed distally of the lateral opening 330. Both the proximal and distal sections 328a, 328b of the looped segment 328 are disposed proximally of the distal end 326b of the hollow shaft 326 when the looped segment 328 is in the contracted configuration, as shown in FIG. 5A. When the looped segment 328 is in the dilated configuration, the proximal section 328a of the looped segment 328 is disposed proximally of the distal end 326b of the hollow shaft 326, whereas a majority, e.g., at least about half, of the distal segment 328b is disposed proximally of the distal end 326b of the hollow shaft 326. As such, a majority of the looped segment 328 is disposed alongside the lateral side 332 of the hollow shaft 326 throughout the transition of the looped segment 328 between the contracted and dilated configurations.

The looped segment 328 is fabricated from shape memory materials, such as, for example, a nickel-titanium alloy to allow the looped segment 328 to move to its predefined, dilated configuration. Other shape memory materials, such as shape memory plastics are also contemplated. In other embodiments, the looped segment 328 may be fabricated from any suitable biocompatible material including, but not limited to, stainless steel, titanium, silicone, polyimide, polyether block amide, nylon, polycarbonate, or combinations thereof.

In operation, a small incision in the edge of a cornea is made to provide access to an anterior chamber and an anterior surface of a cataractous lens of a patient's eye. A capsulorhexis is made through the anterior surface of a lens capsule of the patient's eye providing surgical access to the cataractous lens. With the snare 312 of the ophthalmic surgical instrument 300 in the contracted configuration, as shown in FIG. 5A, the hollow shaft 326 of the housing 310 is inserted through the corneal incision and the capsulorhexis to position a distal end portion of the hollow shaft 326 in an overlapping arrangement with the anterior surface of the lens, and position the looped segment 328 of the snare 312 adjacent the anterior surface of the lens.

Once the looped segment 328 is in the appropriate position, the first end portion 312a of the snare 312 is advanced distally, thereby transitioning the looped segment 328 from the contracted configuration to the dilated configuration, as shown in FIG. 5B. With the looped segment 328 in the deployed configuration, the snare 312 is rotated about its longitudinal axis "B" (e.g., via rotation of the entire ophthalmic surgical instrument 300 or via a rotation mechanism (not shown)) to rotate the looped segment 328 circumferentially about the lens to encircle the lens and position the looped segment 328 relative to the lens so that the plane defined by the looped segment 328 bisects the lens. Upon rotating the snare 312 to the selected position, the axis "C" defined through the lateral opening 330 in the hollow shaft 326 extends perpendicularly through a center of the eye, whereby the hollow shaft 326 overlaps with the anterior surface of the lens and a majority of the looped segment 328 of the snare 312.

With the looped segment 328 of the snare 312 disposed about the lens, and the hollow shaft 326 overlaying and in contact with the anterior surface of the lens, the looped segment 328 is transitioned from the dilated configuration to the contracted configuration, dividing the lens into two hemispherical sections. During contraction of the looped segment 328 about the lens, the looped segment 328 may exert a proximally-oriented force on a distal pole of the lens. However, since the hollow shaft 326 is in position over the lens, the hollow shaft 326 resists and/or prevents elevation and/or tilting of the distal pole of the lens notwithstanding the proximally-oriented force exerted thereon by the closing snare 312.

After one or more fragmentations of the lens by the ophthalmic surgical instrument 300, the fragmented sections of the cataractous lens may then be removed from the eye using any suitable mechanism, such as, for example, an ultrasonic aspirator.

Figure 6:
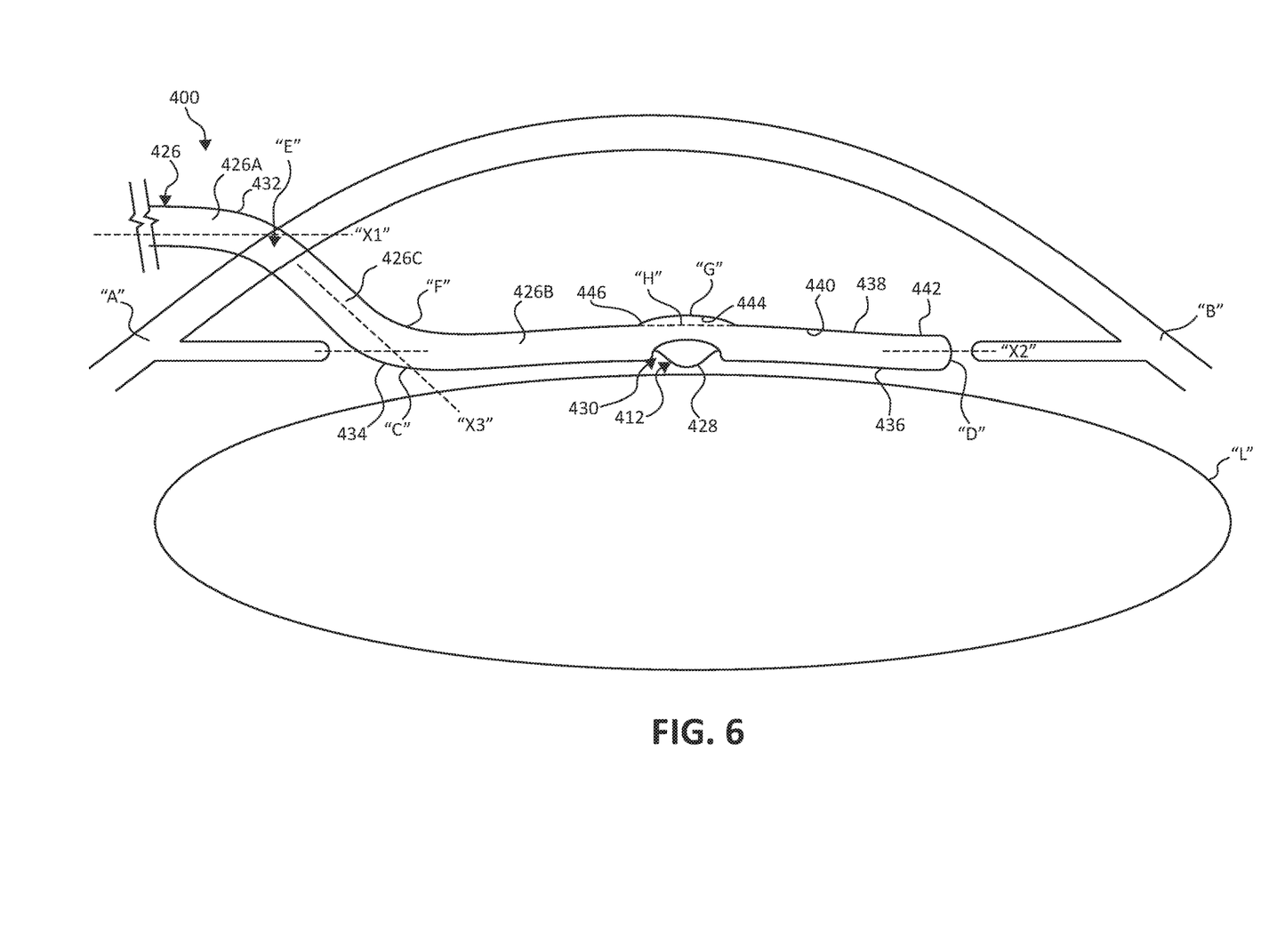
FIG. 6 is a side view of yet another embodiment of an ophthalmic surgical instrument, illustrating a snare thereof in a contracted configuration.

With reference to FIG. 6, another embodiment of an ophthalmic surgical instrument 400 is illustrated, similar to the ophthalmic surgical instrument 300 described above. Due to the similarities between the ophthalmic surgical instrument 400 of the present embodiment and the ophthalmic surgical instrument 300 described above, only those elements of the ophthalmic surgical instrument 400 deemed necessary to elucidate the differences from ophthalmic surgical instrument 300 described above will be described in detail.

The ophthalmic surgical instrument 400 generally includes a housing (not explicitly shown), an elongated shaft 426 extending distally from the housing, and a snare 412 for severing lenticular tissue. The elongated shaft 426 is dimensioned for passage through a corneal incision "E" and has a proximal portion 425 and a distal end portion 426b formed with or otherwise coupled to the proximal portion 425. The proximal portion 425 may include a proximal end portion 426a integrally formed with or attached to the handle housing and an intermediate portion 426c. In aspects, the elongated shaft 426 may be devoid of any intermediate portion, such that the distal end portion 426b bends directly from the proximal end portion 426a. In embodiments, the distal tip of the elongated shaft 426 may be open or closed.

The proximal end portion 426a of the elongated shaft 426 may have a linear configuration and define a central longitudinal axis "X1," and the distal end portion 426b may also be linear and define a central longitudinal axis "X2," that is offset from and parallel with the central longitudinal axis "X1" of the proximal end portion 426a. The distal end portion 426b is angled relative to the proximal portion 425 so that upon entry of the distal end portion 426b into a corneal incision "E," the distal end portion 426b will be positioned flush with the anterior surface "AS" of the lens "L" rather than at an angle, which would otherwise occur if the distal end portion 426b were coaxial with the proximal portion 425. In aspects, the distal end portion 426b or the proximal end portion 426a may assume any suitable configuration. For example, the distal end portion 426b may be curved along its length (e.g., to match a curvature of a lens).

The intermediate portion 426c of the elongated shaft 426 extends between the proximal and distal end portions 426a, 426b, and is angled relative to the proximal and distal end portions 426a, 426b. The intermediate portion 426c may extend between a bent proximal segment 432 of the elongated shaft 426 and a bent distal segment 434 of the elongated shaft 426. The intermediate portion 426c may have a length of about 2 mm between opposite ends "E" and "F" thereof. The intermediate portion 426c has a linear configuration and defines a third central longitudinal axis "X3" that is non-parallel relative to the first and second central longitudinal axes "X1," "X2." In aspects, the central longitudinal axis "X2" of the intermediate portion 426c may be an obtuse angle (e.g., from about 100 degrees to about 170 degrees), an acute angle (e.g., from 10 degrees to about 80 degrees), or a right angle (e.g., about 90 degrees) relative to the first and second central longitudinal axes "X1," "X2."

In aspects, instead of the intermediate portion 426c being linear, the intermediate portion 426c may be curved along its length, bent at various points along its length, or assume any suitable configuration that positions the distal end portion 426b of the elongated shaft 426 on a different plane from the proximal portion 425. In aspects, the intermediate portion 426c may be flexible and/or transitionable between an angled position relative to the proximal and distal end portions 426a, 426b, and a coaxial configuration therewith. In aspects, the intermediate portion 426c or various portions of the elongated shaft 426 may be manually transitionable or fabricated from shape memory material that allows the elongated shaft 426 to transition from an otherwise coaxial configuration into the angled configuration as illustrated.

The distal end portion 426b of the elongated shaft 426 has a length from about 3.5 mm to about 12 mm and, in some aspects, the distal end portion 426b may have a length of about 6 mm or about half the diameter of a cornea measured between points "A" and "B." The distal end portion 426b has a bottom portion 436 configured to be oriented toward a human eye, and an upper portion 438 disposed on an opposite side of the distal end portion 426b. The bottom portion 436 defines an opening 430 therein that is disposed at about a midpoint between opposite ends "C," "D" of the distal end portion 426b. The opening 430 may be configured as an arcuate cutout in the bottom portion 436 of the distal end portion 426b. In aspects, the opening 430 may assume any suitable configuration. The upper portion 438 of the distal end portion 426b has an inner surface 440 and an opposed outer surface 442. The inner surface 440 may form a concave depression 444 and the outer surface 442 may form a convex protuberance 446. The concave depression 444 and the convex protuberance 446 overlap the opening 430. The concave depression 444 provides for more space into which the snare 412 may retract, as will be described.

The snare 412 of the ophthalmic surgical instrument 400 is movable relative to and within the elongated shaft 426 via an actuation mechanism (not shown), similar to the actuation mechanism described above. The snare 412 has a cutting segment, such as, for example, a looped segment 428 configured to protrude out of the opening 430 when the looped segment 428 is in a dilated configuration. It is contemplated that due to the additional space provided by the concave depression 444 in the distal end portion 426b of the elongated shaft 426, the looped segment 428 of the snare 412 may be entirely or substantially received in the elongated shaft 426 when in the contracted configuration. It is contemplated that a distance of about 0.5 mm may be defined between a point "H" of the upper portion 442 and a point "G" of the convex protuberance 446. As such, the looped segment 428 may have about 0.5 mm additional space into which it may retract.

The looped segment 428 defines a length parallel with the central longitudinal axis "X2" defined by the distal end portion 426b of the elongated shaft 426. Due to the length of the opening 430 of the elongated shaft 426 being substantially smaller than the length of the looped segment 428 in the dilated configuration, a majority of the length of the looped segment 428 overlaps with the bottom portion 436 of the elongated shaft 426 when the looped segment 428 is in the dilated configuration. In this way, during use of the ophthalmic surgical instrument 400, the bottom portion 436 of the elongated shaft 426 hangs over a majority of the looped segment 428, such that the elongated shaft 426 sits on a lens "L" during lens fragmentation to prevent upward movement of the lens "L" as the looped segment 428 is constricted thereabout.

In operation, a small incision "E" in the edge of a cornea is made to provide access to an anterior chamber and an anterior surface "AS" of a cataractous lens "L" of a patient's eye. As is typical, the incision "E" is anterior to an anterior surface "AS" of the lens "L." A capsulorhexis is made through the anterior surface of a lens capsule of the patient's eye providing surgical access to the cataractous lens "L."

With the snare 412 of the ophthalmic surgical instrument 400 in the contracted configuration, as shown in FIG. 6, the elongated shaft 426 is inserted through the corneal incision "E" and the capsulorhexis to position the distal end portion 426b of the elongated shaft 426 in an overlapping arrangement with the anterior surface "AS" of the lens "L," and position the looped segment 428 of the snare 412 anterior to a central location of the anterior surface "AS" of the lens "L." Due to the distal end portion 426b being angled relative to the proximal portion 425, the distal end portion 426b is naturally positioned in flush engagement with the anterior surface "AS" of the lens "L" while the proximal portion 425 extends through the incision "E."

Once the looped segment 428 is in the appropriate position, the looped segment 428 is transitioned from the contracted configuration to the dilated configuration, similar to that shown in FIG. 5B. With the looped segment 428 in the deployed configuration, the looped segment 428 of the snare 412 naturally encircles the lens, due to the shape memory material from which the looped segment 428 is fabricated, so that the plane defined by the looped segment 428 bisects the lens. With the looped segment 428 of the snare 412 disposed about the lens "L," and the elongated shaft 426 overlaying and contacting the anterior surface "AS" of the lens "L," the looped segment 428 is transitioned from the dilated configuration to the contracted configuration, dividing the lens into two hemispherical sections.

During contraction of the looped segment 428 about the lens "L," the looped segment 428 may exert a proximally-oriented force on the lens "L." However, since the distal end portion 426b of the elongated shaft 426 is in position over the lens "L," the elongated shaft 426 resists and/or prevents elevation and/or tilting of the lens "L" notwithstanding the proximally/anteriorly-oriented force exerted thereon by the closing snare 412. If the proximal and distal end portions 426a, 426b of the elongated shaft 426 were coaxial instead of being disposed on different planes, the distal end portion 426b would be set at an upward angle relative to the lens "L," which would result in an unevenly dispersed force being exerted on the lens "L" during contraction of the looped segment 428 about the lens "L."

It will be understood that various modifications may be made to the embodiments disclosed herein. Therefore, the above description should not be construed as limiting, but merely as exemplifications of various embodiments. Those skilled in the art will envision other modifications within the scope and spirit of the claims appended thereto.

The invention claimed is:

1. An ophthalmic surgical instrument for severing a lens of an eye, comprising:
   an elongated shaft including:
      a proximal end portion; and
      a distal end portion defining an opening, the distal end portion being offset from the proximal end portion; and
   a snare extending along the elongated shaft and including a cutting segment disposed adjacent the opening and configured to move between a contracted configuration and a dilated configuration, in which the cutting segment assumes a diameter approximating a diameter and shape of a lens, wherein the cutting segment is configured to sever the lens upon moving toward the contracted configuration, wherein the elongated shaft further includes an intermediate portion extending between the proximal and distal end portions, the intermediate portion being angled relative to the proximal and distal end portions, wherein the proximal end portion defines a first longitudinal axis, the distal end portion defines a second longitudinal axis that is parallel with the first longitudinal axis.

2. The ophthalmic surgical instrument according to claim 1, wherein the elongated shaft has a bent proximal segment and a bent distal segment, the intermediate portion extending between the bent proximal and distal segments.

3. The ophthalmic surgical instrument according to claim 1, wherein the intermediate segment is curved or linear.

4. The ophthalmic surgical instrument according to claim 1, wherein the proximal end portion defines a first longitudinal axis and the distal end portion defines a second longitudinal axis that is parallel and out of alignment with the first longitudinal axis.

5. The ophthalmic surgical instrument according to claim 1, wherein the distal end portion has a length from about 3.5 mm to about 12 mm.

6. The ophthalmic surgical instrument according to claim 5, wherein the distal end portion has a length of about 6 mm.

7. The ophthalmic surgical instrument according to claim 1, wherein the distal end portion has a bottom portion configured to be oriented toward a human eye, and an upper portion, the bottom portion defining the opening therein.

8. The ophthalmic surgical instrument according to claim 7, wherein the upper portion has a concave inner surface overlapping the looped segment and the opening.

9. The ophthalmic surgical instrument according to claim 1, wherein the opening has a length that is less than about half of a length of the cutting segment when the cutting segment is in the dilated configuration.

10. The ophthalmic surgical instrument according to claim 9, wherein a majority of the length of the cutting segment is disposed out of alignment with the opening when the cutting segment is in the dilated configuration.

11. An ophthalmic surgical instrument for severing a lens of an eye, comprising:
   a handle;
   an elongated shaft extending distally from the handle and including a distal end portion defining an opening, the distal end portion being angled relative to a proximal portion of the elongated shaft that is disposed proximally of the distal end portion; and
   a snare operably coupled to the housing and including a looped segment configured to move between a contracted configuration and a dilated configuration, in which the looped segment assumes a diameter approximating a diameter and shape of a lens, wherein the looped segment is configured to sever the lens upon moving toward the contracted configuration, wherein the distal end portion has a bottom portion configured to be oriented toward a human eye, and an upper portion, the bottom portion defining the opening therein, the upper portion having a concave inner surface overlapping the looped segment and the opening.

12. The ophthalmic surgical instrument according to claim 11, wherein the distal end portion is bent relative to the proximal portion.

13. The ophthalmic surgical instrument according to claim 11, wherein the proximal portion includes:
   a proximal end portion coupled to the handle; and
   an intermediate portion disposed between and interconnecting the proximal end portion and the distal end portion.

14. The ophthalmic surgical instrument according to claim 13, wherein the distal end portion is bent relative to the intermediate portion.

15. The ophthalmic surgical instrument according to claim 14, wherein the intermediate portion is bent relative to the proximal end portion in an opposite direction as the distal end portion is bent relative to the intermediate portion.

16. The ophthalmic surgical instrument according to claim 11, wherein the opening has a length that is less than about half of a length of the looped segment when the looped segment is in the dilated configuration.

17. The ophthalmic surgical instrument according to claim 11, wherein a majority of the length of the looped segment is disposed out of alignment with the opening when the looped segment is in the dilated configuration.

* * * * *